US008741654B2

(12) United States Patent
Bodie et al.

(10) Patent No.: US 8,741,654 B2
(45) Date of Patent: Jun. 3, 2014

(54) COMPOSITIONS AND METHODS FOR IMPROVED PROTEIN PRODUCTION

(75) Inventors: Elizabeth A. Bodie, San Carlos, CA (US); Steve Sungjin Kim, Fremont, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/494,889

(22) Filed: Jun. 12, 2012

(65) Prior Publication Data

US 2012/0244576 A1 Sep. 27, 2012

Related U.S. Application Data

(62) Division of application No. 12/376,558, filed as application No. PCT/US2007/019072 on Aug. 28, 2007, now Pat. No. 8,216,844.

(60) Provisional application No. 60/840,750, filed on Aug. 29, 2006.

(51) Int. Cl.
*C12N 15/80* (2006.01)

(52) U.S. Cl.
USPC ......... 435/484; 424/93.5; 435/69.1; 435/71.1

(58) Field of Classification Search
None
See application file for complete search history.

(56) References Cited

U.S. PATENT DOCUMENTS

| 4,472,504 | A | 9/1984 | Gallo |
| 4,683,195 | A | 7/1987 | Mullis et al. |
| 4,762,788 | A | 8/1988 | Warzywoda et al. |
| 4,797,361 | A | 1/1989 | Montenecourt |
| 6,255,115 | B1 | 7/2001 | Beijersbergen et al. |
| 6,768,001 | B2 | 7/2004 | Saloheimo et al. |
| 7,713,725 | B2 | 5/2010 | England et al. |

FOREIGN PATENT DOCUMENTS

| EP | 0 215 594 A2 | 3/1987 |
| WO | WO 2005/118795 A2 | 12/2005 |

OTHER PUBLICATIONS

Altschul, et al., "Local alignment statistics", Methods Enzymol, 1996, 266:460-80.
Altschul, S.F. et al. "Basic local alignment search tool." J. Mol. Biol 215(3): 403-410, 1990.
Bajar, A. et al. "Identification of a fungal cutinase promoter that is inducible by a plant signal via a phosphorylated trans-acting factor." PNAS 88(18): 8208-8212, 1991.
Boel, E. et al. "Two different types of intervening sequences in the glucoamylase gene from *Aspergillus niger*." EMBO J. 3(7): 1581-1585, Jul. 1984.
Botstein, D. et al. "Strategies and applications of in vitro mutagenesis." Science 229(4719): 1193-201, Sep. 20, 1985.
Brigidi, P. et al. "Genetic transformation of intact cells of *Bacillus subtilis* by electroporation." FEMS Microbiology Letters 67(1-2): 135-138, 1990.
Broothaerts, W. et al. "Gene transfer to plants by diverse species of bacteria." Nature 433(7026): 629-633, Feb. 10, 2005.
Constans, A. "Rethinking clinical proteomics." The Scientist 19(18): 20-21, 2005.
Dayhoff, M.O. et al. "A Model of Evolutionary Change in Proteins." In Atlas of Protein Sequence and Structure, edited by M.O. Dayhoff, 5 supp. 3: pp. 345-352. Silver Spring, MD: National Biomedical Research Foundation, 1978.
Gelvin, S.B. "Agricultural biotechnology: Gene exchange by design." Nature 433(7026): 583-584, Feb. 10, 2005.
Goldman, G. H. et al. "Transformation of *Trichoderma harzianum* by high-voltage electric pulse." Current Genetics 17(2): 169-174, Feb. 1, 1990.
Gouka, R.J. et al. "Transformation of *Aspergillus awamori* by Agrobacterium tumefaciens-mediated homologous recombination." Nat Biotech 17(6): 598-601, Jun. 1999.
Hajdukiewicz, et al., "The small, versatile pPZP family of Agrobacterium binary vectors for plant transformation", Plant Mol Biol, 1994, 25:989-94.
Higuchi, R. et al. "A general method of in vitro preparation and specific mutagenesis of DNA fragments: study of protein and DNA interactions." Nucleic Acids Research 16(15): 7351-67, Aug. 11, 1988.
Ho, S.N. et al. "Site-directed mutagenesis by overlap extension using the polymerase chain reaction." Gene 77(1): 51-9, Apr. 15, 1989.
Hood, E.E. et al. "New Agrobacterium helper plasmids for gene transfer to plants." Transgenic Research 2(4): 208-218, Jul. 1, 1993.
Hopwood, D. A. "The isolation of mutants." In Methods in microbiology, edited by J.R. Norris et al., 3A: pp. 363-433. New York: Academic Press, 1970.
Horton, R.M. et al. "Engineering hybrid genes without the use of restriction enzymes: gene splicing by overlap extension." Gene 77(1): 61-68, Apr. 15, 1989.
Iglesias, A. et al. "Plasmid transformation in *Bacillus subtilis*: Symmetry of gene conversion in transformation with a hybrid plasmid containing chromosomal DNA." Molecular and General Genetics MGG 189(1): 73-76 Feb. 1, 1983.
Ilmen, M. et al. "Regulation of cellulase gene expression in the filamentous fungus *Trichoderma reesei*." Appl. Environ. Microbiol. 63(4): 1298-1306, Apr. 1, 1997.
Innis, M. A. et al. "Expression, Glycosylation, and Secretion of an Aspergillus Glucoamylase by *Saccharomyces cerevisiae*." Science 228(4695): 21-26, Apr. 5, 1985.
Liu, Y.-G. et al. "Thermal asymmetric interlaced PCR: automatable amplification and sequencing of insert end fragments from P1 and YAC clones for chromosome walking." Genomics 25(3): 674-681, Feb. 10, 1995.

(Continued)

*Primary Examiner* — John Ulm
(74) *Attorney, Agent, or Firm* — Danisco US Inc.

(57) ABSTRACT

The present invention relates to the identification of novel nucleic acid sequences, designated herein as 7p, 8k, 7E, 9G, 8Q and 203, in a host cell which effect protein production. The present invention also provides host cells having a mutation or deletion of part or all of the gene encoding 7p, 8k, 7E, 9G, 8Q and 203, which are presented in FIG. 1, and are SEQ ID NOS.: 1-6, respectively. The present invention also provides host cells further comprising a nucleic acid encoding a desired heterologous protein such as an enzyme.

9 Claims, 4 Drawing Sheets

(56) References Cited

OTHER PUBLICATIONS

Liu, Y.-G. et al. "Efficient isolation and mapping of *Arabidopsis thaliana* T-DNA insert junctions by thermal asymmetric interlaced PCR." The Plant Journal 8(3): 457-463, 1995.

Lo, K.-M. et al. "Specific amino acid substitutions in bacterioopsin: Replacement of a restriction fragment in the structural gene by synthetic DNA fragments containing altered codons." PNAS 81(8): 2285-2289 Apr. 1984.

Lorito, M. et al. "Biolistic transformation of *Trichoderma harzianum* and *Gliocladium virens* using plasmid and genomic DNA." Current Genetics 24(4): 349-356, Oct. 1, 1993.

Mullaney, E.J. et al. "Primary structure of the trpC gene from *Aspergillus nidulans*." Molecular and General Genetics MGG 199(1): 37-45, Apr. 1, 1985.

Mullins, E.D. et al. "Agrobacterium-Mediated Transformation of *Fusarium oxysporum*: An Efficient Tool for Insertional Mutagenesis and Gene Transfer." Phytopathology 91(2): 173, 2001.

Needleman, S.B. et al. "A general method applicable to the search for similarities in the amino acid sequence of two proteins." J. Mol. Biol 48(3): 443-53, Mar. 1970.

Nunberg, J.H. et al. "Molecular cloning and characterization of the glucoamylase gene of *Aspergillus awamori*." Mol. Cell. Biol. 4(11): 2306-2315, Nov. 1, 1984.

Pearson, W.R. et al. "Improved Tools for Biological Sequence Comparison." Proc. Natl. Acad. Sci. USA 85(8): 2444-2448, Apr. 15, 1988.

Penttilä, M. et al. "A versatile transformation system for the cellulolytic filamentous fungus *Trichoderma reesei*." Gene 61(2): 155-64, 1987.

Sarkar, G. et al. "The "megaprimer" method of site-directed mutagenesis." BioTechniques 8(4): 404-7, Apr. 1990.

Schulein, M. "Cellulases of *Trichoderma reesei*." Methods in enzymology 160: 234-242, 1988.

Sessions, A. et al. "A High-Throughput *Arabidopsis* Reverse Genetics System." Plant Cell 14(12): 2985-2994, Dec. 1, 2002.

Shimada, Atsushi. "PCR-Based Site-Directed Mutagenesis." In In Vitro Mutagenesis Protocols, edited by M.K. Trower, pp. 157-165. Methods in Molecular Biology 57. http://dx.doi.org/10.1385/0-89603-332-5:157. New York: Humana Press, 1996.

Shpaer, E.G. "GeneAssist. Smith-Waterman and other database similarity searches and identification of motifs." Methods Mol. Biol 70: 173-87, 1997.

Smith, J.L. et al. "Sequence of the cloned pyr4 gene of *Trichoderma reesei* and its use as a homologous selectable marker for transformation." Current Genetics 19(1): 27-33, Jan. 1, 1991.

Smith, T.F. et al. "Comparison of biosequences." Adv. Appl. Math 2: 482-489, 1981.

Timberlake, W.E. "Cloning and Analysis of Fungal Genes." In More Gene Manipulations in Fungi, edited by J.W. Bennett et al., pp. 70-76. San Diego, CA: Academic Press, 1991.

Toyama, et al., "Successive construction of cellulase hyperproducers of *Trichoderma* using hyperpolyploids", Appl Biochem Biotechnol, 2000, 84-86: 419-429.

Yelton, M.M. et al., "Transformation of *Aspergillus nidulans* by using a trpC plasmid", Proc. Natl. Acad. Sci., 1984,81:1470-4.

Youngman, et al., "Genetic transposition and insertional mutagenesis in *Bacillus subtilis* with *Streptococcus faecalis* transposon Tn917", Proc Natl acad Sci, 1983, 80:2305-9.

International Search Report and the Written Opinion of the International Searching Authority for International Patent Application No. PCT/US2007/019072 dated Jul. 3, 2008.

Keranan, et al., "Production of recombinant proteins in the filamentous fungus *Trichoderma reesi*", Curr Opin Biotechnol, (1995), 6:534-7.

Miettinen-Oinonen, A, et al., "Enhanced production of cellobiohydrolases in *Trichoderma reesei* and evaluation of the new preparations in biofinishing of cotton", J Biotechnol, (2005), 116:305-17.

Punt, et al., "Filamentous fungi as cell factories for heterologous protein production", Trends in Biotechnol, (2002), 20:200-6.

Toyama, et al., "Construction of cellulase hyper-producers of *Trichoderma reesei* Rut C-30 for utilization for waste paper using colchicine and benomyl", J Mol Catalysis B: Enzymatic, (2002), 17:175-8.

Toyama, et al., "Construction of cellulase hyperproducing strains derived from polyploids and *Trichoderma reesei*", Microbios, (1999), 100:7-18.

FIG. 1

SEQ ID NO: 1
T. reesei gene 7p (corresponding to scaffold_4
1263425 to 1263463 bp in T. reesei genomic sequence)
GAGGTCTGAGACCGCGAGTCTTGCTGCAGCTTGTGGGCTCCTGTCGTGCCAGCAAGTACTCAGCGCGC
AGGTACTGCATACCTC SEQ ID NO.:2
T. reesei gene 8k (corresponding to scaffold_4
229869 to 229952 bp in T. reesei genomic sequence)
AAGCCGCACGTGCCGAGTCACATGGCCGGCACCAGCGCAGCGTCACCGCCCTCGCTTAGCTCCCACAC
TTTGAGGGCGGCAGAA SEQ ID NO.:3
T. reesei gene 7E  (corresponding to scaffold _45  34303 to 34663
bp in T. reesei genomic sequence)
CGGCATGGCCTTGGACCTCTATTCAGGTATTATTACTGTTTCGCCCTTTGTTTTCCTGCTCTTCTGCT
CTGTCTTTCCTTCCTCGCCCAAAGTACCGCGGCCTCCATGCAAGTACCCCAAGTACCTCGAGTGACTT
CAGGTACGCCAAGCCCCGAGCTGTCTGATAGGCCAGGACCCGCCAGGGCCAGACATGCGCCAGGGCAC
AGCCAATCAAAGGCCGCAATGGCTGCCACCAACGCCGAGTTGTCCGTGTCGACTAACGACCGTGGCCA
GGGATGCTGGGCTTTTAGGTGCCTTTTGGAGCTGCTGGGAGAGGTGAGAAAAGGGCGGGGGTTTCCTG
TCATGGTGGTGTGGGCGGCAA SEQ ID NO.:4
T. reesei gene 9G (corresponding to scaffold _45
34613 to 34675 bp in T. reesei genomic sequence)
GGCTGGCATTTCCGGCATGGCCTTGGACCTCTATTCAGGTATTATTACTGTTTCGCCCTTTGCTTCTC
CACTA SEQ ID NO.:5
T. reesei gene 8Q  (corresponding to scaffold _
2 1068666 to 1069118 bp in T. reesei genomic sequence)
CCTTGCAGCCACAGCCCGGCGCCCACGCTGGGACGGGAACCAAGAGGCACAGTCAAGCCCACAGCCG
TGGCCTTGCGGATAACATCACCCGACTTGCAGCCTGCTTCGGCGACGACGAAGGCAAGGGCACTGGA
GTGACAATTTTCCCCATCTACCTCAGCAGGGAGAATATGCACCTGATCAAAAGCTTCCATGTCGACT
GCAACAACATGAGACCAGAGACAGTGTCCGCTGTGGCCCCCTCCAACGACAGTCAGTCCAACTCGGT
GCTTCAGAGCCCACCGAACGCACTGCTGGACGTGTGGAATCCCCGTCGGTCTGACAACCGCCGCGGG
ACGGTGGAGACGAGCCTCCCAATTCTTGATCTTCTTGTCCCCTTTGGCCAAAGGCACCTGTTGCTCC
AGCTCATGAAGCATTGTCGCGTGATGTGTGAAAGCCATCATGACGTCGGGC SEQ ID NO.:6
T. reesei gene 203  (corresponding to scaffold _ 32
84112 to  84517  bp in T. reesei genomic sequence)
GCCGGCTGTTGGTGTCGAGCTCAGGAATGGCTCCTCCTGGCTTCCGCTGTGGTGATGGCAGAGCAAGC
AAGCCCTTTCATCTTAGTCTGGGCTCGTCAGATGGCTCGCTTGGCAGAGTATAAGCCACAATGAATCC
AAGGTGAGTATGATCCAACACATACCCTGCCTAGGAGGCACTGCTATGTACATGGCAGTTCCAAAGTA
CCGTAACTTGGAAGGTCTTTTAGCATGGAAGACTTGGAACAGGCTGTCAACAGATTACACGTGGATAC
CTCACAAACTGACTTAGTATAAGTTAAGGAGAACCATGTTTGGTATCCATCATCGAGAAGGACAAGAC
CAGAATTGTCTTGGACAAATGCTAATGTAGCTACCCGCCTCAGCTGTGTTCCGCAACAGGGCAAGG FIG. 2
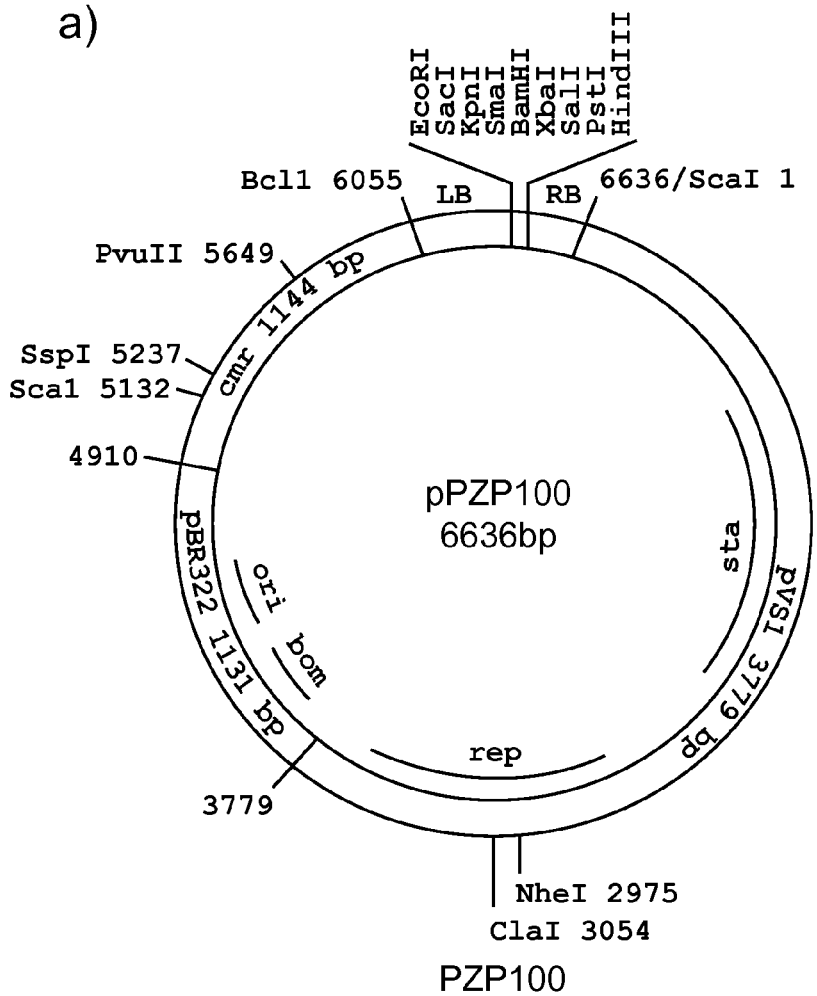
a)
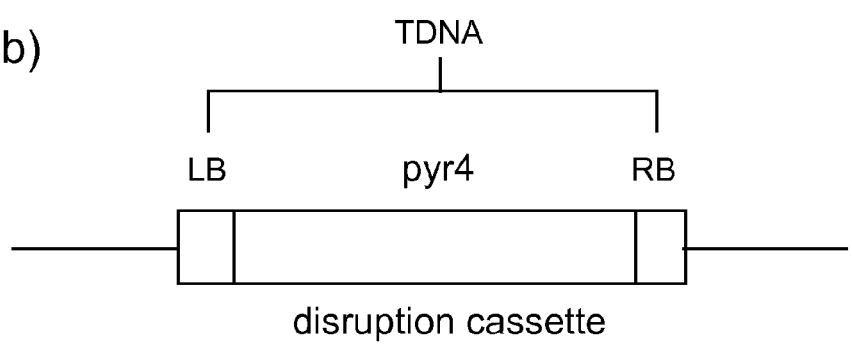
b)

SEQUENCE LISTING

```
<160> NUMBER OF SEQ ID NOS: 14

<210> SEQ ID NO 1
<211> LENGTH: 84
<212> TYPE: DNA
<213> ORGANISM: trichoderma reesei

<400> SEQUENCE: 1
gaggtctgag accgcgagtc ttgctgcagc ttgtgggctc ctgtcgtgcc agcaagtact    60
cagcgcgcag gtactgcata cctc                                          84

<210> SEQ ID NO 2
<211> LENGTH: 84
<212> TYPE: DNA
<213> ORGANISM: trichoderma reesei

<400> SEQUENCE: 2
aagccgcacg tgccgagtca catggccggc accagcgcag cgtcaccgcc ctcgcttagc    60
tcccacactt tgagggcggc agaa                                          84

<210> SEQ ID NO 3
<211> LENGTH: 361
<212> TYPE: DNA
<213> ORGANISM: trichoderma reesei

<400> SEQUENCE: 3
cggcatggcc ttggacctct attcaggtat tattactgtt tcgcccttttg ttttcctgct    60 cttctgctct gtctttcctt cctcgcccaa agtaccgcgg cctccatgca agtaccccaa   120
gtacctcgag tgacttcagg tacgccaagc cccgagctgt ctgataggcc aggacccgcc   180
```

```
agggccagac atgcgccagg gcacagccaa tcaaaggccg caatggctgc caccaacgcc    240
gagttgtccg tgtcgactaa cgaccgtggc cagggatgct gggcttttag gtgccttttg    300
gagctgctgg gagaggtgag aaaagggcgg gggtttcctg tcatggtggt gtgggcggca    360
a                                                                   361
```

<210> SEQ ID NO 4
<211> LENGTH: 73
<212> TYPE: DNA
<213> ORGANISM: trichoderma reesei

<400> SEQUENCE: 4

```
ggctggcatt tccggcatgg ccttggacct ctattcaggt attattactg tttcgccctt     60
tgcttctcca cta                                                        73
```

<210> SEQ ID NO 5
<211> LENGTH: 453
<212> TYPE: DNA
<213> ORGANISM: trichoderma reesei

<400> SEQUENCE: 5

```
ccttgcagcc acagcccggc gcccacgctg ggacgggaac caagaggcac agtcaagccc     60
acagccgtgg ccttgcggat aacatcaccc gacttgcagc ctgcttcggc gacgacgaag    120
gcaagggcac tggagtgaca attttcccca tctacctcag cagggagaat atgcacctga    180
tcaaaagctt ccatgtcgac tgcaacaaca tgagaccaga cagtgtcc gctgtggccc      240 cctccaacga cagtcagtcc aactcggtgc ttcagagccc accgaacgca ctgctggacg    300
tgtggaatcc ccgtcggtct gacaaccgcc gcggacggt ggagacgagc ctcccaattc     360
ttgatcttct tgtccccttt ggccaaaggc acctgttgct ccagctcatg aagcattgtc    420
gcgtgatgtg tgaaagccat catgacgtcg ggc                                 453
```

<210> SEQ ID NO 6
<211> LENGTH: 406
<212> TYPE: DNA
<213> ORGANISM: trichoderma reesei

<400> SEQUENCE: 6

```
gccggctgtt ggtgtcgagc tcaggaatgg ctcctcctgg cttccgctgt ggtgatggca     60
gagcaagcaa gcccttcat cttagtctgg gctcgtcaga tggctcgctt ggcagagtat     120
aagccacaat gaatccaagg tgagtatgat ccaacacata ccctgcctag gaggcactgc    180
tatgtacatg gcagttccaa gtaccgtaa cttggaaggt cttttagcat ggaagacttg     240
gaacaggctg tcaacagatt acacgtggat acctcacaaa ctgacttagt ataagttaag    300
gagaaccatg tttggtatcc atcatcgaga aggacaagac cagaattgtc ttggacaaat    360
gctaatgtag ctacccgcct cagctgtgtt ccgcaacagg gcaagg                   406
```

<210> SEQ ID NO 7
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1, 11
<223> OTHER INFORMATION: n = A,T,C or G

<400> SEQUENCE: 7

```
ngtcgaswga nawgaa                                                   16

<210> SEQ ID NO 8
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 5, 10
<223> OTHER INFORMATION: n = A,T,C or G

<400> SEQUENCE: 8
tgwgnagsan casaga                                                   16

<210> SEQ ID NO 9
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 5, 10
<223> OTHER INFORMATION: n = A,T,C or G

<400> SEQUENCE: 9
agwgnagwan cawagg                                                   16

<210> SEQ ID NO 10
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 5, 10, 13
<223> OTHER INFORMATION: n = A,T,C or G

<400> SEQUENCE: 10
wgtgnagwan canaga                                                   16

<210> SEQ ID NO 11
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 11
agccgcggcc tcctgat                                                  17

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 12
gtcggcgctc aggcacaggt tgg                                           23

<210> SEQ ID NO 13
<211> LENGTH: 19
<212> TYPE: DNA
<213> ORGANISM: Artificial Sequence
```

-continued

```
<220> FEATURE:
<223> OTHER INFORMATION: synthetic oligonucleotide

<400> SEQUENCE: 13
cgtcgccgtc tcgctcctg                                              19

<210> SEQ ID NO 14
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 14
tgcgggagga agaggagtag gaac                                        24
```

COMPOSITIONS AND METHODS FOR IMPROVED PROTEIN PRODUCTION

CLAIM OF PRIORITY

This application is a divisional application of U.S. application Ser. No. 12/376,558, filed Jul. 16, 2010, now U.S. Pat. No. 8,216,844, which is a U.S. National Phase Application of International Application No. PCT/US2007/019072, filed Aug. 28, 2007, which claims the benefit of provisional application No. 60/840,750 filed on Aug. 29, 2006, the contents of which are hereby incorporated by reference in their entireties.

GOVERNMENT SUPPORT

Portions of this work were funded by Subcontract No. ZCO-30017-01 with the National Renewable Energy Laboratory under Prime Contract No. DE-AC36-99GO10337 with the U.S. Department of Energy. Accordingly, the United States Government may have certain rights in this invention.

SEQUENCE LISTING

The sequence listing submitted via EFS, in compliance with 37 C.F.R. §1.52(e), is incorporated herein by reference. The sequence listing text file submitted via EFS contains the file "919-D1_seqlist.txt" created on Jun. 8, 2012, which is 8,192 bytes in size.

FIELD

The invention relates to novel host cells with improved protein production, methods of producing such host cells and uses thereof.

INTRODUCTION

Enzyme washing is commonly used as a wet process technique to improve textile handling, appearance and other surface characteristics of, e.g., cottons and cotton blends in the industry. One example of the successful application of enzyme technology in the textile industry is the replacement of traditional stone washing (which is very time consuming and labor intensive) in denim processing by cellulase washing. Hydrolysis of cellulase, a major component of cotton, with cellulase is useful for the biopolishing of cotton fabrics, which enhances their aesthetic performance by cleavage of glycosidic bonds in cellulose molecules. Cellulases are important industrial enzymes used, for example, in the processing of textiles and in detergents. Cellulases are enzymes that hydrolyze cellulose (e.g., α-1,4-D-glucan linkages) and produce as primary products glucose, cellobiose and cellooligosaccharides. The cellulases used in the textile industry are produced by several different microorganisms and comprise several different enzyme classifications including those identified as exo-cellobiohydrolases (CBH), endoglucanases (EG) and β-glucosidases (BG) (M. Schulein, Methods in Enzymology, vol. 160, pp. 235-242 (1988)).

Therefore, cellulases, and components thereof, either individually or in combination, are useful in treating textiles. Additional benefits to using cellulases to treat cotton-containing fabrics include the removal of sizing from the fabric (sizing is a composition used to stiffen fabric so it is easier to handle in the manufacture of, for example, garments) removing fuzz and pills from the surface of the fabric and giving a stone-washed appearance and feel to the fabric. Still, improvements in the effectiveness and efficiency of cellulase treatment of fabrics will be beneficial to the garment and textile industries as well as other industries such as in the manufacture of detergents and in the manufacturing of fuel ethanol from biomass.

Despite intensive research related to the use of cellulases in industrial processes, cellulases known and used in the art have shown significant drawbacks. For example, many cellulases have been problematic due to low activity, poor alkaline or acid stability, poor temperature stability and poor oxidative stability. More importantly, cellulase production by microorganisms is often low and, therefore, inefficient from a commercial standpoint. Therefore, what is needed are new strains of microorganisms and new nucleotide sequences that improve the efficiency of cellulase production.

SUMMARY

The applicants have discovered that disruption of specific nucleotide sequences in a host cell results in improved production or a desired protein by such modified host cells. The applicants have also identified molecular basis responsible for the improved protein production. Accordingly, the invention features novel host cells suitable for the enhanced production of a desired polypeptide compared to the parent strain, methods of producing a desired polypeptide from the said host cells and the specific disrupted nucleotide sequences (SEQ ID NOS.: 1-6) responsible for the improvements in production of a desired polypeptide.

In a first embodiment there is provided a modified host cell. The modified host cell may be a fungi or a bacterium. The modified host cell comprises deletion or disruption of specific nucleotide sequences that results in the improved expression and/or secretion of a desired polypeptide. The specific nucleotide sequence that may be disrupted is selected from 7p, 8k, 7E, 9G, 8Q and 203, which are presented in FIG. 1, and are SEQ ID NOS.: 1-6, respectively, or sequences having 80%, 85%, 90%, 95%, 96%, 97%, 98%, or 99% sequence identity to any one of SEQ ID NOs:1-6, or sequences that have been codon optimized for the specific host cell. In one aspect the fungi is a filamentous fungi. In a further aspect, the filamentous fungi is selected from Trichoderma, e.g., Trichoderma reesei, Trichoderma viride, Trichoderma koningii, Trichoderma harzianum; Penicillium sp.; Humicola sp., including Humicola insolens; Chrysosporium sp., including C. lucknowense; Gliocladium sp.; Aspergillus sp.; Fusarium sp., Neurospora sp., Hypocrea sp., and Emericella sp. In another aspect there is provided a host cell that has had the endogenous genes disrupted or genes corresponding to the nucleotides provided for herein provides improved protein production over the parent host cell strain (i.e., an unmodified host cell).

In one embodiment there is provided a host cell having a mutation or deletion of part or all of a gene having the sequence selected from at least one sequence set forth in any one of SEQ ID NOs:1-6, and said mutation or deletion results in the enhanced production of a desired polypeptide compared to the parent host cell.

In an aspect, the host cell is a filamentous fungus. In another aspect, the desired protein may be a homologous or heterologous to the host cell. In a further aspect the heterologous proteins may be selected from the group consisting of hormones, enzymes, growth factors, and cytokines. In a yet further aspect, the enzyme is selected from the group consisting of proteases, carbohydrases, lipases, isomerases, racemases, epimerases, tautomerases, mutases, transferases, kinases and phosphatases.

In a second embodiment there is provided a method for the production of a heterologous protein in a transformed filamentous fungus host cell comprising the steps of:

(a) obtaining a filamentous fungus host cell comprising a nucleic acid encoding said heterologous protein wherein said host cell contains a mutation or deletion in at least one nucleic acid sequence having the sequence set forth in any one of SEQ ID NOs:1-6, wherein said mutation or deletion results in the enhanced production of the heterologous protein compared to a parent filamentous fungus: and (b) growing said filamentous fungus host cell under conditions suitable for the expression of said heterologous protein.

In certain aspects the nucleic acid that is mutated or deleted is at least SEQ ID NO:1 or SEQ ID NO:2. In a third embodiment there is provided an isolated nucleotide sequence selected from a group consisting of SEQ ID NOs: 1-6. In one aspect the nucleotide sequence has been modified. The modification may be selected from truncation, deletion, mutation or other means of inactivation. Also provided herein are vectors comprising at least one isolated nucleotide sequence selected from a group consisting of SEQ ID NOs: 1-6 wherein the nucleotide sequence has been modified.

In a fourth embodiment there is provided a method of producing a modified host cell said method comprising:

(a) obtaining a parental host cell strain
(b) transforming said parental cell strain with the vector comprising at least one isolated nucleotide sequence selected from a group consisting of SEQ ID NOs: 1-6 wherein the nucleotide sequence has been modified,
(c) selecting modified host cells wherein said modified host cells produce more homologous protein than the parental host cell.

In a fifth embodiment there is provided a method of producing a heterologous desired polypeptide said method comprising:

(a) obtaining a parental host cell strain
(b) transforming said parental cell strain with a vector encoding a desired polypeptide;
(c) transforming said parental cell strain with a vector comprising at least one isolated nucleotide sequence selected from a group consisting of SEQ ID NOs: 1-6 wherein the nucleotide sequence has been modified to produce a modified host cell
(d) selecting modified host cells that produce said heterologous desired polypeptide wherein steps (b) and (c) may be done in any order or simultaneously. The suitable sterile growth medium additionally comprises an inducer of cellulase production selected from one or more of cellulose, lactose, sophorose and glucose/sophorose. The method may additionally comprises the at least partial purification of cellulases produced by said culture.

In a sixth embodiment there is provided a method for the producing a novel strain of *T. reesei* using insertional mutagenesis wherein said novel strain of *T. reesei* has superior total protein or cellulase production as compared to the parent strain of *T. reesei*, comprising:

(a) preparing a population of competent *Agrobacterium* sp., cells by electroporating into competent *Agrobacterium* sp., cells an expression vector comprising, in operable condition, the left and right T-DNA boarder regions, pV51 plasmid origins for replication in *Agrobacterium* sp. and bacterial markers to confer resistance to chloramphenicol to create a population comprising transformed *Agrobacterium* sp., cells;

(b) selecting for *Agrobacterium* from said population of step (a);
(c) inoculating a culture of *T. reesei* spores with the *Agrobacterium* sp. transformants of step (b) to create an induction culture;
(d) culturing said induction culture of step (c) at about 18° C. and for about 24 hours to create a population comprising;
(e) transferring samples of said population of transformed *T. reesei* of step (d) to selective medium and isolating colonies of *T. reesei* effective in degrading cellulose; and
(f) comparing the effectiveness of cellulose degradation between the *T. reesei* of the isolated colonies of step (e) and the non-transformed parent strain, wherein said *T. reesei* of the isolated colonies of step e are superior to in cellulose degradation when compared to the non-transformed parent strain. The *Agrobacterium* sp, cells are selected from *Agrobacterium tumefaciens* and *Agrobacterium rhizogenes*.

DRAWINGS

FIG. 1, shows the nucleic acid sequences of SEQ ID NO.: 1 of *T. reesei* 8k and SEQ ID NO.: 2 from *T. reesei* 7p and SEQ ID No: 3 from *T. reesei* 7E, SEQ ID NO 4: from *T. reesei* 9G, SEQ. NO. 5 from *T. reesei* 8Q and SEQ NO. 6 from *T. reesei* 203.

FIG. 2 (*a*) shows an expression vector used for the transfection of T-DNA border regions into *Agrobacterium*. FIG. 2 (*b*) shows the pyr4 disruption contained within the expression vector of FIG. 2 (*a*).

DESCRIPTIONS OF VARIOUS EMBODIMENTS

Figure 3:
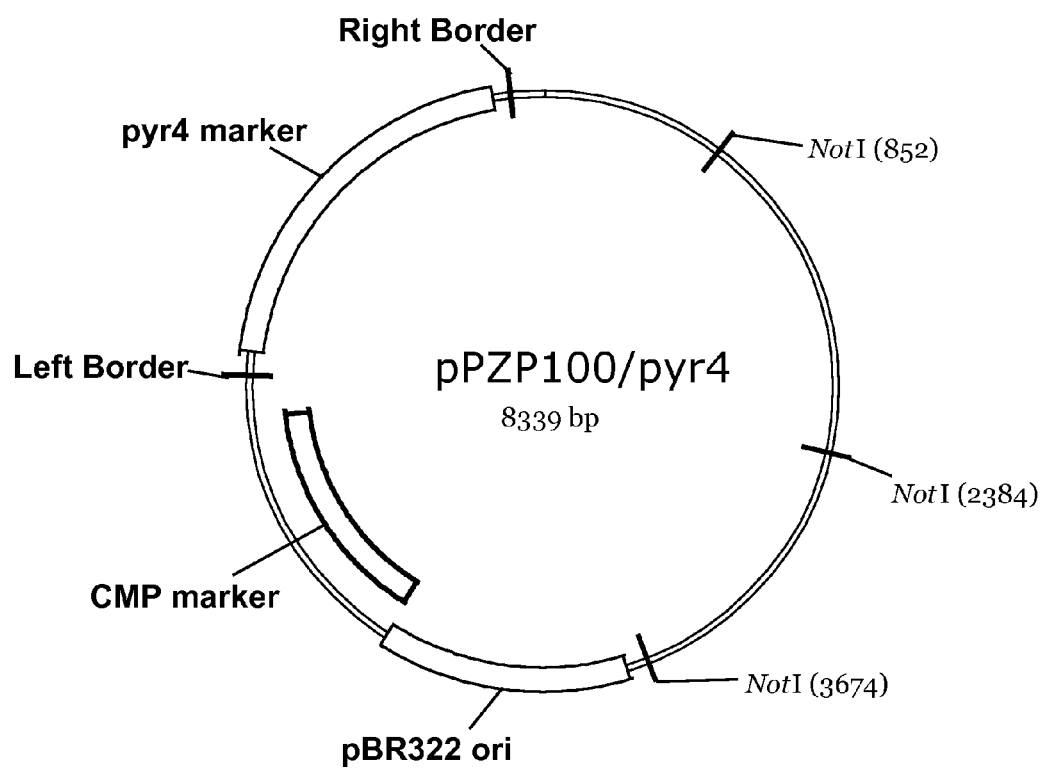
FIG. 3 is a schematic for the pPZP100/pyr4 vector.
Figure 4:
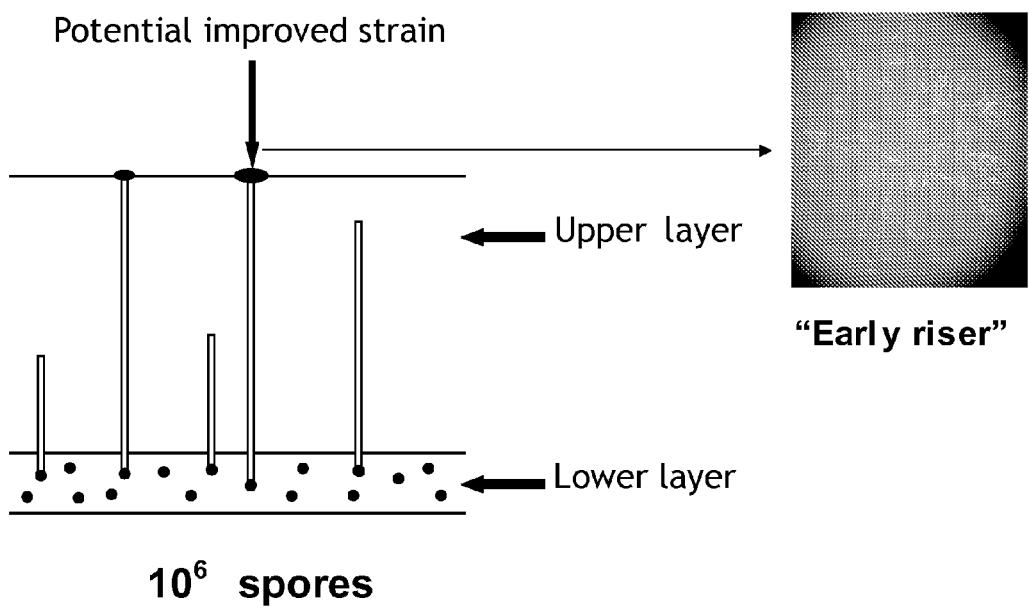
FIG. 4 shows a representation of spore growth in the Toyama screen.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

A "polypeptide of interest", "protein of interest", "desired polypeptide" and "desired protein" are used interchangeably herein.

The terms "protein(s)" and "polypeptide(s)" are used interchangeably herein. The conventional one-letter or three-letter code for amino acid residues is used herein.

A "heterologous promoter," as used herein is a promoter which is not naturally associated with a gene, gene portion or a purified nucleic acid.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

A "purified preparation of cells," as used herein, refers to, in the case of plant or animal cells, an in vitro preparation of cells and not an entire intact plant or animal In the case of cultured cells or microbial cells, it consists of a preparation of at least 10% and more preferably 50% of the subject cells as a portion of the total number of cells.

In the context of the present invention the term "biologically pure" is defined as having substantially, e.g., the above mentioned *T. reesei* strains as the only living organism in the culture or the predominant living organism in the culture and that the culture is substantially free of other living organisms. The culture need not be 100% free of other organisms providing the other organisms do not substantially interfere with the growth of the *T. reesei* strains of the present invention.

The ability to culture *T. reesei* for the production of cellulase enzymes is known in the art as is exemplified in the Examples section, infra, and in U.S. Pat. Nos. 4,797,361, 4,762,788 and 4,472,504.

A "substantially pure nucleic acid," e.g., a substantially pure DNA, RNA, etc., is a nucleic acid which is one or both of: 1) not immediately contiguous with either one or both of the sequences, e.g., coding sequences, with which it is immediately contiguous (i.e., one at the 5' end and one at the 3' end) in the naturally-occurring genome of the organism from which the nucleic acid is derived; or 2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences.

The term "heterologous" with reference to a polynucleotide or protein refers to a polynucleotide or protein that does not naturally occur in a host cell. In some embodiments, the protein is a commercially important industrial protein. It is intended that the term encompass proteins that are encoded by naturally occurring genes, mutated genes, and/or synthetic genes. The term "homologous" with reference to a polynucleotide or protein refers to a polynucleotide or protein that occurs naturally in the host cell.

"Cellulase," "cellulolytic enzymes" or "cellulase enzymes" means bacterial, or fungal exoglucanases or exocellobiohydrolases, and/or endoglucanases, and/or β-glucosidases. These three different types of cellulase enzymes act synergistically to convert cellulose and its derivatives to glucose.

Many microbes make enzymes that hydrolyze cellulose, including the wood rotting fungus *Trichoderma*, the compost bacteria *Thermomonospora*, *Bacillus*, and *Cellulomonas*; *Streptomyces*; and the fungi *Trichoderma*, *Humicola*, *Aspergillus* and *Fusarium*. The enzymes made by these microbes are mixtures of proteins with three types of actions useful in the conversion of cellulose to glucose: endoglucanases (EG), cellobiohydrolases (CBH), and beta-glucosidase.

The term "reverse genetics," as defined herein, refers to a strategy to determine a particular gene's function by studying the phenotypes with alterations in the gene of interest. In other words, after obtaining the strain with a desired phenotype, e.g., altered morphology, an investigation to determine the genetic change responsible for the phenotype is undertaken. Various techniques can be used for reverse genetics including the use of transposons and REMI (Restriction-enzyme-mediated integration). This differs from classical wherein one tries to determine the phenotype resulting from genetic change. To learn the influence a sequence has on phenotype, or to discover its biological function, researchers can engineer a change or disruption in the DNA. After this change has been made a researcher can look for the effect of such alterations in the whole organism. In the present invention, insertional mutagenesis has been done by transforming in the pyr4 gene into *T. reesei*. In most cases, a single copy of the pyr 4 gene integrates randomly into the *T. reesei* genome disrupting the gene(s) that is present at that site. Since the sequence of the pyr 4 gene is know, it acts as a tag and can be used to detect any genetic changes that has been made. In this case, pyr4 is also used as a homologous selectable marker for the transformation of *T. reesei* (Smith, et al., Sequence of the cloned pyr4 gene of *Trichoderma reesei* and its use as a homologous selectable marker for transformation. Curr. Gen, 19:27-33, 1991). Other methods can be used to create disruptions in DNA for reverse genetics screens including random deletions, insertions and point mutations, directed deletions and point mutations, gene silencing and interference using transgenes.

The term "T-DNA" as defined herein, refers to sequences of DNA common to *Agrobacterium* that facilitates the transfer of DNA into plant genomes. T-DNA is used by molecular biologists to permit the transfer of selected DNA into a plant genome for the purpose of, for example, creating insertional mutants for the purpose of performing reverse genetics. In nature, the T-DNA of *Agrobacterium* facilitates the transfer of DNA into a plant host causing crown gall disease. For the purposes of transformation, only the border regions of the T-DNA sequences are used thereby permitting the insertion of desired DNA sequences. In the present invention, pyr4 genes were inserted into the *T. reesei* genome using T-DNA border sequences.

As used herein, "microorganism" refers to a bacterium, a fungus, a virus, a protozoan, and other microbes or microscopic organisms.

As used herein, "derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. For example, the nucleotide sequences of the present invention (SEQ ID NOs.: 1-6) are the *T. reesei* genomic sequences that are the borders of the insertional point of the pyr4 gene and represent the gene(s) that has been disrupted in the *T. reesei* genome.

As used herein, "percent (%) sequence identity" with respect to the amino acid or nucleotides sequences identified herein is defined as the percentage of amino acid residues or nucleotides in a candidate sequence that are identical with the amino acid residues or nucleotides in a sequence, after aligning the sequences and introducing gaps, if necessary, to achieve the maximum percent sequence identity, and not considering any conservative substitutions as part of the sequence identity. Methods for performing sequence alignment and determining sequence identity are known to the skilled artisan, may be performed without undue experimentation, and calculations of identity values may be obtained with definiteness. See, for example, Ausubel, et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman, et al., (1970) J. Mol. Biol. 48:443; the local homology algorithm of Smith, et al., (1981) Adv. Appl. Math. 2:482; the search for similarity method of Pearson et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see, Altschul, et al., (1990) J. Mol. Biol. 215:403-410). Computerized programs using these algorithms are also available, and include, but are not limited to: ALIGN or Megalign (DNASTAR) software, or WU-BLAST-2 (Altschul, et al., Meth. Enzym., 266:460-480 (1996)); or GAP, BESTFIT, BLAST Altschul, et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues and may be 30, 40, 50 or more amino acid residues. Corrections for increased sequence identity associated with inclusion of gaps in the derivative's amino acid sequence can be made by assigning gap penalties.

The term "% homology" is used interchangeably herein with the term "% identity"

Exemplary computer programs which can be used to determine identity between two sequences include, but are not limited to, the suite of BLAST programs, e.g., BLASTN, BLASTX, and TBLASTX, BLASTP and TBLASTN, and are publicly available on the Internet (see, for example, the BLAST page on the National Center for Biotechnology Information website). See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

As used herein, "expression vector" means a DNA construct including a DNA sequence which is operably linked to a suitable control sequence capable of affecting the replication, disruption, or expression of the DNA in a suitable host. Such control sequences may include origins of replication or a promoter to affect transcription, an optional operator sequence to control transcription, a sequence encoding suitable ribosome-binding sites on the mRNA, and sequences which control termination of transcription and translation. Different cell types are preferably used with different expression vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and preferred promoters for *Trichoderma reesei* are reesei cbh1, cbh2, eg1, eg2, eg3, eg5, xln1 and xln2 promoters. The vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing or replicating the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC19 and their derivatives, wider host range plasmids, e.g., RP4, phage DNAs e.g., the numerous derivatives of phage λ, e.g., NM989, and other DNA phages, e.g., M13 and filamentous single stranded DNA phages, yeast plasmids such as the 2μ plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook, et al., MOLECULAR CLONING: A LABORATORY MANUAL, SECOND EDITION, Cold Spring Harbor Press (1989). Often, such expression vectors including the DNA sequences of the invention are transformed into a unicellular host by direct insertion into the genome of a particular species through an integration event (see, e.g., Bennett & Lasure, MORE GENE MANIPULA- TIONS IN FUNGI, Academic Press, San Diego, pp. 70-76 (1991) and articles cited therein describing targeted genomic insertion in fungal hosts).

"pPZP100," as used herein, refers to 1) an expression vector that can be transformed into *T. reesei*, and also 2) a shuttle vector that can be amplified in *E. coli* and *Agrobacterium*. See, for example, Hajdukiewiez et al. (1994) Plant Mol. Bio. 25:989-994.

As used herein, "host strain" or "host cell" means a suitable host for an expression vector including DNA according to the present invention. Host cells useful in the present invention are generally prokaryotic or eukaryotic hosts, including any transformable microorganism in which expression can be achieved. Specifically, host strains may be *Bacillus subtilis, Escherichia coli, Trichoderma reesei, Saccharomyces cerevisiae* or *Aspergillus niger*. Host cells are transformed or transfected with vectors constructed using recombinant DNA techniques.

A "modified cell" or "modified strain" means a cell or strain that has been modified by having one of the nucleic acid sequences described herein deleted or inactivated (e.g., disrupted).

An "inactivated gene" means locus of a genome that, prior to its inactivation, was capable of producing a protein, i.e., capable of being transcribed into an RNA that can be translated to produce a full length polypeptide. A gene is inactivated when it is not transcribed and translated into full length catalytically active protein. A gene may be inactivated by altering a sequence required for its transcription, by altering a sequence required for RNA processing, e.g., poly-A tail addition by altering a sequence required for translation, for example. A deleted gene, a gene containing a deleted region, a gene containing a rearranged region, a gene having an inactivating point mutation or frameshift and a gene containing an insertion are types of inactivated gene. A gene may also be inactivated using antisense or any other method that abolishes expression of that gene.

As used herein, "functionally attached" or "operably linked" means that a regulatory region, such as a promoter, terminator, secretion signal or enhancer region is attached to or linked to a structural gene and controls the expression of that gene.

As used herein, a substance (e.g., a polynucleotide or protein) "derived from" a microorganism means that the substance is native to the microorganism.

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma reesei, Trichoderma viride, Trichoderma koningii, Trichoderma harzianum; Penicillium* sp.; *Humicola* sp., including *Humicola insolens; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus*, or *Aspergillus nidulans* cell.

In another preferred embodiment, the filamentous fungal parent cell is a *Trichoderma reesei* cell.

"*Trichoderma*" or "*Trichoderma* sp." refers to any fungal strains which have previously been classified as *Trichoderma* or which are currently classified as *Trichoderma*. Preferably the species are *Trichoderma reesei* or *Trichoderma viride*.

The term "equivalent" refers to nucleotide sequences encoding functionally equivalent polypeptides or functionally equivalent polypeptides; Equivalent nucleotide sequences will include sequences that differ by one or more nucleotide substitutions, additions or deletions, such as allelic variants, and include sequences that differ from a native or natural nucleotide due to the degeneracy of the genetic code.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The practice of the present invention will employ, unless otherwise indicated, conventional techniques of cell biology, cell culture, molecular biology, transgenic biology, microbiology, recombinant DNA and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover, ed., 1985); *Oligonucleotide Synthesis* (M. J. Gait, ed., 1984); Mullis, et al., U.S. Pat. No. 4,683,195; *Nucleic Acid Hybridization* (B. D. Hames & S. J. Higgins, eds., 1984); *Transcription And Translation* (B. D. Hames & S. J. Higgins, eds., 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos, eds., 1987, Cold Spring Harbor Laboratory); *Methods In Enzymology*, Vols. 154 and 155 (Wu, et al., eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986;)). Also, information regarding methods of preparation, expression, isolation and use of proteases may be obtained by review of U.S. Pat. No. 6,768,001. Terms not defined within this document either specifically, by reference or by context are to have definitions common in the art at the time of filing.

Other features and advantages of the invention will be apparent from the following detailed description, and from the claims.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook, et al., 1989, and Ausubel, F M, et al., 1993, for definitions and terms of the art. It is to be understood that this invention is not limited to the particular methodology, protocols, and reagents described, as these may vary.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The applicants have identified the disrupted nucleotide sequences responsible for the increased production of proteins, including but not limited to cellulose. The nucleotide sequences are referred to as 7p, 8k, 7E, 9G, 8Q and 203 from T. reesei, which are presented in FIG. 1, and are SEQ ID NOS.: 1-6, respectively Likewise, it is contemplated that the nucleotide sequences of the present invention are used in screening assays for the detection of, e.g., other strains of T. reesei or other microorganisms effective in protein production or for homologs and sequence variants of the sequences of the present invention.

It is a preferred embodiment of the present invention that the novel T. reesei strains of the present invention are used in methods for the production of proteins wherein the proteins may be heterologous or homologous to the host cell. For example, a method is contemplated wherein a suitable sterile growth medium is inoculated with one or more strains of T. reesei selected from the group consisting of T. reesei strains that have had at least one nucleotide sequence selected from 7p, 8k, 7E, 9G, 8Q and 203 deleted or inactivated and the inoculated growth medium is incubated under conditions which will permit the growth of said T. reesei strain. The present invention is not limited to any particular growth/culture medium. Any complex or defined medium that supports growth and is conductive of protein production and in particular cellulase production is suitable. Examples include media disclosed in WO 2005/118795 or media disclosed in Ilmen, M., Saloheimo, A., Onnela, M., and Penttila, M. E., 1997, App Environ Microbiol 63, 1298-1306. In a preferred embodiment, 100 mM PIPPS (Calbiochem) was included to maintain the pH at 5.5. Also, the present invention is not limited to any particular culture method (e.g., batch culture, continuous flow culture, etc.). It is further contemplated that the sterile growth medium may additionally comprise an inducer of cellulase production. Non-limiting examples of suitable inducers are cellulose, lactose, sophorose and glucose/sophorose. In an embodiment the inducer of cellulase production is glucose/sophorose as described in US Publication Number US-2004-0121446.

It is also an embodiment of the present invention that the cellulases (in the form of "whole cellulase") produced by the T. reesei strains of the present invention are purified from the culture medium.

Reverse Genetics

One of the objectives of much of genetic research is to identify the genes responsible for selected phenotypic traits. While much effort is being undertaken to develop genomic information from a large number of organisms, often the information about the function of a gene is more important than the information as to the sequence of the gene itself. One way in which the function of individual genes is studied is to look for mutated versions of the gene of interest. Sometimes the search for mutated versions of a gene and the study of the mutated genes is referred to as "reverse genetics." If one finds a gene which is mutated so as to render the mutated gene inoperative, one can discern what phenotypic change has been make to the organism that renders it different from organisms not carrying the mutated version of the gene.

Various strategies have been developed for using reverse genetics to study the functioning of genes. For example, one laboratory at the University of Wisconsin has created a large population of Arabidopsis plant lines each of which had been transformed using the transferred-DNA (T-DNA) from the bacteria Agrobacterium tumefaciens, which has the native ability to transfer T-DNA into the genome of the plant cell.

In the present invention, a large population of T. reesei fungal lines has been created to screen for mutant strains with increased cellulase production. The techniques used were based on work by Sessions, et al., (A high-throughput Arabidopsis reverse genetics system, The Plant Cell, 14:2985-2994 (2002)). In the present invention, the pyr4 gene was transfected into T. reesei using Agrobacterium T-DNA border sequences to cause disruptions of the genomic DNA. The transformants were then screened for strains that showed increased cellulase production as compared to the parent T. reesei strain and as exemplified below.

Molecular Biology

The techniques of molecular biology are used in the present invention for the purpose of identifying and isolating mutant strains of T. reesei that have increased effectiveness in the production of cellulases over the parent strain.

In one embodiment this invention provides for the identification of genes and gene mutations of Trichoderma reesei that confer an increase in cellulase productivity to T. reesei. Therefore, this invention relies on routine techniques in the field of recombinant genetics and reverse genetics (discussed above and in the Examples section). Basic texts disclosing the general methods of use in this invention include Sambrook, et al., Molecular Cloning, A Laboratory Manual (2nd ed. 1989); Kriegler, Gene Transfer and Expression: A Laboratory Manual (1990); and Ausubel, et al., eds., Current Protocols in Molecular Biology (1994).

In one embodiment of the present invention, disruption libraries of T. reesei were prepared by transforming in the pyr4 gene using Agrobacterium tumefaciens-mediated transformation. In another embodiment, Agrobacterium rhizogenes is used for the transformation protocols. In yet another embodiment, the bacterium used for the transformation protocol is any species of Agrobacterium (Agrobacterium sp.) suitable for the purpose. Other bacterial strains useful for insertional mutagenesis are known to those skilled in the art. See for example, Constans, A. (2005) The Scientist 19(5):32; Broothaerts et al. (2005) Nature 433:629-633; and Gelvin, S B (2005) Nature 433:583-584. FIG. 2 exemplifies a suitable expression vector. In one embodiment, the expression vector used serves a dual function in that it is capable of being replicated in E. coli and in Agrobacterium using ColE1 and pVS1 plasmid origins for replication, respectively. The expression vector used in the present invention was pPZP100 but one practiced in the art will understand that other vectors and other plasmid origins of replication are known in the art and are also effective for these purposes. Those skilled in the art are also aware that a natural plasmid origins of replication can be modified by replacement, substitution, addition or elimination of one or more nucleotides without changing its function or can be replaced with other effective plasmid origins of replication. The practice of the invention encompasses and is not constrained by such alterations to or replacement of the plasmid origins of replication or by the use of other plasmids, origins of replication or transfection methods known in the art at the time of this invention or by their equivalents.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. However, exemplary promoters are the *Trichoderma reesei* cbh1, cbh2, eg1, eg2, eg3, eg5, xln1 and xln2 promoters.

In addition to a promoter sequence, the expression cassette should also contain a transcription termination region downstream of the structural gene to provide for efficient termination. The termination region may be obtained from the same gene as the promoter sequence or may be obtained from different genes.

Although any fungal terminator is likely to be functional in the present invention, preferred terminators include: the terminator from *Aspergillus nidulans* trpC gene (Yelton, M., et al., (1984) PNAS USA 81:1470-1474, Mullaney, E. J., et al., (1985) MGG 199:37-45), the *Aspergillus awamori* or *Aspergillus niger* glucoamylase genes (Nunberg, J. H., et al., (1984) Mol. Cell Biol. 4:2306, Boel, E., et al., (1984) EMBO J. 3:1581-1585) and the *Mucor miehei* carboxyl protease gene (EPO Publication No. 0 215 594).

The particular expression vector used to transport the genetic information into the cell is not particularly critical. Any of the conventional vectors used for *Agrobacterium* transformation expression in plants and other eukaryotic cells may be used. Suitable vectors include, but are not limited to, the pPZP family of *Agrobacterium* binary vectors (as described in Hjdukiewiez et al 1994. Plant Molecular biology 25: 989-994), pCAMBIA 1300 (as described in Mullins, E. D. et al 2001. Phytopathology 91:173-180), pUR5755 (as described in Gouka, R. K. et al 1999. Nature biotechnology 17: 598-601) and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*. For *Agrobacterium* transformation it is necessary to use sequences that allow replication in both *E. coli* and *Agrobacterium* as well as the left and right borders of the *Agrobacterium* Ti plasmid. Non-limiting examples of suitable sequences are given in the Examples section, infra.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologous protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood, et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138.

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of protease gene promoter sequences. Large batches of transformed cells can be cultured as described in Example 2, infra. Finally, product is recovered from the culture using standard techniques.

Thus, the invention herein provides for the expression and enhanced secretion of desired polypeptides whose expression is under control of gene promoter sequences including naturally occurring protease or cellulase genes, fusion DNA sequences, and various heterologous constructs. The invention also provides processes for expressing and secreting high levels of such desired polypeptides.

Host Cells

In certain embodiments, the cell is a filamentous fugal cell having a genome comprising an inactivated gene, where the inactivated gene that comprises a nucleotide sequence that is least 95% identical to any of SEQ ID NOs:1-6.

Genes may be inactivated in a fungal cell using a number of methods, including methods that employ antisense molecules, RNA interference, or ribozymes, for example. In certain embodiments, however, expression of the genes may be reduced by gene inactivation.

A subject fungal cell may be constructed using any convenient method, for example, by altering the sequence of a gene of the cell by making an insertion, deletion, replacement, or rearrangement in the gene for example. The portion of the gene to be altered may be, for example, the coding region or a regulatory element required for expression of the coding region. An example of such a regulatory or control sequence of a gene may be a promoter sequence or a functional part thereof, i.e., a part which is necessary for expression of the gene.

In one embodiment, the subject fungal cell may be constructed by gene deletion methods. Gene deletion techniques enable the partial or complete removal of the gene thereby eliminating their expression. In such methods, the deletion of the gene may be accomplished by homologous recombination using a plasmid that has been constructed to contiguously contain the 5' and 3' regions flanking the gene.

In another embodiment, the subject fungal cell may be constructed by introducing, substituting, and/or removing one or more nucleotides in the gene or a regulatory element thereof required for the transcription or translation thereof. For example, nucleotides may be inserted or removed so as to result in the introduction of a stop codon, the removal of the start codon, removal of a splice cite, or a frame-shift of the open reading frame. Such a modification may be accomplished by site-directed mutagenesis or PCR generated mutagenesis in accordance with methods known in the art. See, for example, Botstein and Shortie, 1985, Science 229: 4719; Lo et al., 1985, Proceedings of the National Academy of Sciences USA 81: 2285; Higuchi et al., 1988, Nucleic Acids Research 16: 7351; Shimada, 1996, Meth. Mol. Biol. 57: 157; Ho et al., 1989, Gene 77: 61; Horton et al., 1989, Gene 77: 61; and Sarkar and Sommer, 1990, BioTechniques 8: 404.

In another embodiment, the subject fungal cell may be constructed by gene disruption techniques by inserting into the gene of interest an integrative plasmid containing a nucleic acid fragment homologous to the gene which will create a duplication of the region of homology and incorporate vector DNA between the duplicated regions. Such gene disruption can eliminate gene expression if the inserted vector separates the promoter of the gene from the coding region or interrupts the coding sequence such that a non-functional gene product results. A disrupting construct may be simply a selectable marker gene accompanied by 5' and 3' regions homologous to the gene. The selectable marker enables identification of transformants containing the disrupted gene.

In another embodiment, the subject fungal cell may be constructed by the process of gene conversion (see, for example, Iglesias and Trautner, 1983, Molecular General Genetics 189: 73-76). For example, in the gene conversion method, a nucleotide sequence corresponding to the gene(s) is mutagenized in vitro to produce a defective nucleotide sequence which is then transformed into the parent strain to produce a defective gene. By homologous recombination, the defective nucleotide sequence replaces the endogenous gene.

In an alternative embodiment, the subject fungal cell may be constructed using random or specific mutagenesis using methods that include, but are not limited to, chemical mutagenesis (see, for example, Hopwood, The Isolation of Mutants in Methods in Microbiology (J. R. Norris and D. W. Ribbons, eds.) pp 363-433, Academic Press, New York, 1970) and insertional mutagenesis, such as transposition (see, for example, Youngman et al., 1983, Proc. Natl. Acad. Sci. USA 80: 2305-2309). Modification of the gene may be performed by subjecting the parent strain to mutagenesis and screening for mutant strains in which expression of the gene has been reduced or eliminated. The mutagenesis, which may be specific or random, may be performed, for example, by use of a suitable physical or chemical mutagenizing agent, for example.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosogaunidine (NTG) O-methyl hydroxylamine, nitrous acid, ethyl methane sulphonate (EMS), sodium bisulphite, formic acid, and nucleotide analogues. When such agents are used, the mutagenesis is typically performed by incubating the parent strain to be mutagenized in the presence of the mutagenizing agent of choice under suitable conditions, and selecting for mutants exhibiting reduced or no expression of a gene.

As noted above, the subject fungal cell may be a filamentous fungal cell. In certain embodiments, the cell may be non-pathogenic, i.e., non-pathogenic to humans. In particular embodiments, the cells may be filamentous fungal cells of a strain that has a history of use for production of proteins that has GRAS status, i.e., a Generally Recognized as Safe, by the FDA.

In particular embodiments, the subject fungal cell may be a cell of the following species: *Trichoderma*, (e.g., *Trichoderma reesei* (previously classified as *T. longibrachiatum* and currently also known as *Hypocrea jecorina*), *Trichoderma viride*, *Trichoderma koningii*, and *Trichoderma harzianum*)); *Penicillium* sp., *Humicola* sp. (e.g., *Humicola insolens* and *Humicola grisea*); *Chrysosporium* sp. (e.g., *C. lucknowense*), *Gliocladium* sp., *Aspergillus* sp. (e.g., *Aspergillus oryzae*, *Aspergillus niger*, *Aspergillus nidulans*, *Aspergillus kawachi*, *Aspergillus aculeatus*, *Aspergillus japonicus*, *Aspergillus sojae*, and *Aspergillus awamori*), *Fusarium* sp., *Neurospora* sp., *Hypocrea* sp., or *Emericella* sp. (See also, Innis et al., (1985) Sci. 228:21-26), among others. In some embodiments, subject fungal cells may be strains of *Aspergillus niger* which include ATCC 22342, ATCC 44733, ATCC 14331 and strains derived therefrom. In some embodiments, a host cell may be one wherein native genes have been deleted or inactivated. For example genes corresponding to protease genes or genes corresponding to cellulase genes may be inactivated.

In one embodiment, the subject fungal cell may contain a recombinant nucleic acid for expression of a protein in the cell. The protein may be not native to the cell (i.e., heterologous) or native to the cell (i.e., endogenous to the cell). The protein may be expressed using a number of different protocols, e.g., by use of an expression cassette for production of the protein, by operably linking a nucleic acid encoding the protein to a promoter that is part of the genome of the cell with another promoter, or by replacing the promoter that is part of the genome of the cell, for example.

The DNA sequences of several fungal genes and the proteins encoded by those genes have been determined and deposited into NCBI's Genbank database, including the complete genomes of *Aspergillus fumigatus*, *Candida glabrata*, *Cryptococcus neoformans*, *Debaryomyces hansenii*, *Encephalitozoon cuniculi*, *Eremothecium gossypii*, *Gibberella zeae*, *Kluyveromyces lactis*, *Magnaporthe grisea*, *Neurospora crassa*, *Pichia stipitis*, *Saccharomyces cerevisiae* (baker's yeast), *Schizosaccharomyces pombe* (fission yeast), *Ustilago maydis* and *Yarrowia lipolytica*. Further sequences may be found at the US Department of Energy Joint Genome Institute's *Trichoderma reesei* and *Aspergillus niger* genome sequence databases (as found at the world wide website of jgi.doe.gov).

In certain embodiments, a subject gene may comprise a nucleotide sequence that is at least 70% (e.g., at least 80%, at least 90%, at least 95%, at least 97% or at least 98% sequence identity) to any of SEQ ID NOS:1-6; or b) may hybridize under stringent conditions to any of SEQ ID NOS:1-6.

Protein of Interest or Desired Protein

The terms protein of interest and desired protein may be used interchangeably herein. The present invention is particularly useful in enhancing the intracellular and/or extracellular production of proteins. The protein may be homologous or heterologous. Proteins that may produced by the instant invention include, but are not limited to, hormones, enzymes, growth factors, cytokines, antibodies and the like.

Hormones include, but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 ($\alpha$ and $\beta$), IL-2 through IL-13) and the interferons ($\alpha$, $\beta$ and $\gamma$).

Human Interleukin-3 (IL-3) is a 15 kDa protein containing 133 amino acid residues. IL-3 is a species specific colony stimulating factor which stimulates colony formation of megakaryocytes, neutrophils, and macrophages from bone marrow cultures.

Antibodies include, but are not limited to, immunoglobulins from any species from which it is desirable to produce large quantities. It is especially preferred that the antibodies are human antibodies. Immunoglobulins may be from any class, i.e., G, A, M, E or D.

Additionally, a "protein of interest" or "polypeptide of interest" refers to the protein to be expressed and secreted by the host cell. The protein of interest may be any protein that up until now has been considered for expression in prokaryotes. In one embodiment, the protein of interest which is expressed and secreted include proteins comprising a signal peptide. The protein of interest may be either homologous or heterologous to the host. Thus, a protein of interest may be a secreted polypeptide particularly an enzyme which is selected from amylolytic enzymes, proteolytic enzymes, cellulolytic enzymes, oxidoreductase enzymes and plant wall degrading enzymes. Examples of these enzymes include amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. The secreted polypeptide may also be a hormone, a growth factor, a receptor, vaccine, antibody or the like. In an embodiment the secreted polypeptide is a cellulolytic enzyme.

Industrial Applications of the Invention

The present invention has many practical applications in industry, as is contemplated herein, this description is intended to be exemplary, and non-inclusive. The *T. reesei* strains of the present invention are more effective in cellulase production over the parent strain and, as such, are useful in the efficient production of cellulases that are useful in various industries as exemplified below.

In several embodiments, cellulase produced by the *T. reesei* strains of the present invention have contemplated use in ethanol production, baking, fruit juice production, brewing, distilling, wine making, leather, oils and fats, paper and pulp and the animal feed production.

In other embodiments, the present invention has contemplated is the active "biological" component of detergents and cleaning products. Here, cellulases are used to break down various stains and other acquired contaminants Embodiments of the invention include testing the compatibility of enzymes with detergent ingredients by doing stability studies and testing them in a variety of formulations.

In another embodiment, the cellulases produced by the *T. reesei* strains of the present invention have contemplated use in the textile industry, mainly in the finishing of fabrics and garments. Major applications include: desizing, removal of size, (that is, removal of stiff elements of fiber), from threads in fabrics after weaving. For example, the cellulases produced by the present invention can be used in bio-polishing, a process to reduce or eliminate pilling tendency and to give fabrics a smoother and glossier appearance, and in bio-stoning, a process that can replace traditional pumice stones used in stonewashing of denim to achieve a worn look.

In yet another embodiment, the present invention has contemplated enzymatic uses for the liquefaction and saccharification of starch into glucose and isomerisation into fructose. The cellulases produced by the present invention may be used to convert large volumes of corn and other grains into sweeteners, like high fructose corn syrup and maltose syrup.

It will be apparent to those skilled in the art to which this invention pertains that other embodiments of the present invention may be performed based on the teachings contained herein. It is intended that such embodiments are contemplated to be included within the scope of the present invention.

EXAMPLES

The present invention is described in further detail in the following examples which are not in any way intended to limit the scope of the invention as claimed in any way. The attached Figures are meant to be considered as integral parts of the specification and description of the invention. All references cited are herein specifically incorporated by reference for all that is described therein. The following examples are offered to illustrate, but not to limit the claimed invention.

In the experimental disclosure which follows, the following abbreviations apply: eq (equivalents); U (units); M (Molar); µM (micromolar); N (Normal); mol (moles); mmol (millimoles); µmol (micromoles); nmol (nanomoles); pmole (pico moles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds), MM (Minimal Medium).

Example 1

*Agrobacterium*-Mediated Transformation Procedures

This Example shows how insertional mutagenesis was performed using *Agrobacterium tumefaciens*-mediated transformation. Likewise, *Agrobacterium rhizogenes* is equally effective for use in the transformation procedure. This procedure allowed the production of mutant libraries of *Trichoderma reesei* that contained strains with single disruption events in the genomic DNA. These disruption events were randomly distributed throughout the genome. Since the disruption was done using a known DNA sequence, it was possible to trace the exact site of disruption and identify the gene(s) that were affected. In this case, the libraries were screened for improved cellulase producers (see, Example 2). In strains 7p, 8k, 7E, 9G, 8Q and 203, the specific disruptive genomic DNA sequences responsible for the improvement in cellulase production were identified.

Disruption libraries of *Trichoderma reesei* were prepared by transforming in the pyr4 gene using *Agrobacterium tumefaciens*-mediated transformation. The disruption library contained about 30,000 transformants. The disruption library was screened using the Toyama method (see, Example 2). This method selects for mutant that are able to utilize and/or grow more efficiently on Avicel (cellulose). In the past, this method has resulted in the isolation of strains with improved yield and productivity. Mutants isolated from the Toyama screen were examined in shake flasks for total protein production. Mutants showing increased protein production of greater that 10% in multiple experiments were considered to be improved. One mutant, 8k, was found to have improved total protein production compared to the parental control. Southern analysis showed that this strain contained only one copy of the pyr4 gene indicating that one disruption event had taken place. The sequence of the *T. reesei* sequence in 8k that was disrupted by the pyr4 gene was determined by thermal asymmetric interlace (tail) PCR. BLAST results were obtained from public databases as well as the *T. reesei* genome database. For 8k, the disrupted sequence immediately after the left border matched bases 1263481-1253276 in scaffold-4 in the *T. reesei* genome database. For 7p, the disrupted sequence immediately after the left border matched bases 229978-229764 in scaffold-4 when BLASTed in the *T. reesei* genome library. The sequence for the other four strains of the present invention were identified similarly.

The *Agrobacterium tumefaciens* strain used for this work was strain EHA 105. EHA 105 is considered to be a hypervirulent strain (Hood, et al., 1993). Other strains are also compatible with the following procedure are, e.g., A136 and EHA 101. Transformation frequencies for these three strains are similar when transforming *T. reesei*. In addition, *A. rhizogenes* (ATCC 43057) or any other rhizogenes strain may be used herein.

The PZP 100-based expression vector was made as follows. The vector contains the left and right T-DNA border regions, a pBR322 bam site for mobilization from *E. coli* to *Agrobacterium*, CalE1 and pVS1 plasmid origins for replication in *E. coli* and *Agrobacterium*, respectively. Bacterial markers confer resistance to amp (Hajdukiewiez, O., et al., 1994). A representation of the vector in shown in FIG. 2.

The *E. coli* vector was made as follows. The expression cassette was prepared by standard molecular biological techniques and ligated into a PZP vector. Preferred strains of *E. coli* are XL gold cells (Invitrogen, Carlsbad, Calif.) and DH5α, which is known in the art. LA plus 25 ppm cmp plates were used to select for *E. coli* transformants. Typically, about 1-10% of the *E. coli* transformants have the desired vector. LB plus 25 ppm cmp was used to grow the *E. coli* containing the vector DNA. Vector DNA was isolated using standard protocols known in the art.

Vector DNA was electroporated into *Agrobacterium* cells as follows. First, competent *Agrobacterium* cells were prepared. *Agrobacterium* cells were revived from cryopreservation by growing on LA medium at 28° C. for about three days. Colonies were selected and grown in Luria-Bertani culture broth (LB; Invitrogen) plus 0.1% glucose in 250 ml dented bottom flasks containing 50 ml medium. The cultures were incubated at 28° C. until growth occurred (about two days). An alternate procedure is to start the culture in a 5 ml culture tube and transfer to the 250 ml flask when growth is noticed. About 10% of the volume (v/v) of the above flask was then transferred into a fresh flask with the same medium. This flask was incubated until an O.D. (at 600 nm) of about 0.4-0.8 was obtained (about 5-6 hours of growth). Next, in the cold, the cells were spun down in a centrifuge at 10,000 rpm for 10 minutes. The cells were then washed 3× in cold 1 M HEPES, pH 7.0. Next, the cells were washed once in cold 1 mM HEPES with 10% glycerol. Aliquots of 50-100 ml were froze at −70° C. Cell viability was determined (typically about $1\times10^9$ CFU/ml after freezing). Competent cells are good for one year or longer when stored at −70° C.

After the generation of competent *Agrobacterium* cells, the cells were transfected by electroporation. Competent *Agrobacterium* calls were thawed on ice. About 40 µl of the cells were mixed with about 1 µg of DNA in a 0.2 cm electroporation cell (on ice). The cells were electroporated at 200 Omnhs, at 25 µF, 2.5 volts with a Buchler 3-150 electroporator. SOC medium (Invitrogen) was added immediately after electroporation into the electroporation tube. (In another embodiment, the *Agrobacterium* cells are electroporated with the ligation mixture thus skipping the *E. coli* step. With this alternate method, 1 µl of the ligation mixture is used in the electroporation step.) After the addition of SOC to the electroporation mixture, dilutions of the mixture were plated onto LA medium plus 250 ppm cmp culture plates and incubated at 28° C. for four days. (In other embodiment, as little at 25 ppm cmp can be used to obtain colonies in a shorter time frame but a larger number of colonies will need to be screened to find ones containing the vector. This is because some *Agrobacterium* strains have some natural resistance to cmp). After electroporation, $1\times10^7$ CFU/ml of *Agrobacterium* transformants were obtained and about 90-100% had the vector as determined by PCR.

*Agrobacterium tumefaciens* EHA 105 (Hajdukiewiez, P., Svab, Z., and Maliga, P. (1994) The small versatile, pPZP family of *Agrobacterium* binary vectors for plant transformation. Plant Molecular Biology 25, 989-994) containing the PZP-pyr4 disruption vector was grown in 50 mL MM medium at 28° C., 200 rpm, for 24 hr. After the 24 hr incubation a 5 mL aliquot was transferred to 50 mL Induction medium and incubated at 28° C., 200 rpm, until the absorbance at 600λ reached 0.8 abs. About 10 ml of this culture was added to 20 ml fresh induction medium along with 10 ml of a P-37 py4⁻ strain that had been grown for 24 hr at 28° C., 200 rpm in YEG (g per liter: yeast extract—5, glucose—20, uridine—2 mg). The viable count of this culture was about $1\times10^6$ CFU/ml. The mixture was incubated statically at 28° C., and sampled at 48, 72, 96, and 144 hr. Samples were washed 3× in sterile water, and plated on Vogels. Colonies that grew were transferred to a second Vogel plate for confirmation. Results are shown in the table below:

TABLE 1

| Incubation time (h) | # transformants isolated on vogels |
|---|---|
| 0 | 0 |
| 48 | 2 |
| 72 | 5 |

TABLE 1-continued

| Incubation time (h) | # transformants isolated on vogels |
|---|---|
| 96 | 7 |
| 144 | 4 |

These results indicate that *Agrobacterium* transformation can be done in a liquid medium when the incubation period is between 48-144 h. The optimal incubation time is between 72-96 h.

TABLE 2

Agrobacterium Induction Medium

Make to one liter:

| $K_3HPO_4$ | 2.05 g |
|---|---|
| $KH_2PO_4$ | 1.45 g |
| NaCl | 0.15 g |
| $MgSO_4*7H_2O$ | 0.5 g |
| $CaCl_2*6H_2O$ | 0.1 g |
| $FeSO_4*7H_2O$ | 0.0025 g |
| $(NH_4)_2SO_4$ | 0.5 g |
| Glucose | 1.8 g |
| Glycerol | 5.0 g |
| Prepare in 40 mM MES buffer | |
| (2-(N-Morpholino)ethanesulfonic acid) pH 5.3 | |
| After sterilization add | |
| 1M acetosyringone | 200 ml |

Agrobacterium Inductive Plate Medium

Make to one liter:

| $K_3HPO_4$ | 2.05 g |
|---|---|
| $KH_2PO_4$ | 1.45 g |
| NaCl | 0.15 g |
| $MgSO_4*7H_2O$ | 0.5 g |
| $CaCl_2*6H_2O$ | 0.1 g |
| $FeSO_4*7H_2O$ | 0.0025 g |
| $(NH4)_2SO_4$ | 0.5 g |
| Glucose | 1.8 g |
| Glycerol | 5.0 g |
| Agar | 15 g |
| Prepare in 40 mM MES pH 5.3 | |
| After sterilization add | |
| 1M acetosyringone | 200 ml |
| 100 mg/ml uridine | 2.5 ml |
| Cool. | |

Agrobacterium Minimal Medium (MM)

Make to one liter:

| $K_3HPO_4$ | 2.05 g |
|---|---|
| $KH_2PO_4$ | 1.45 g |
| NaCl | 0.15 g |
| $MgSO_4*7H_2O$ | 0.5 g |
| $CaCl_2*6H_2O$ | 0.1 g |
| $FeSO_4*7H_2O$ | 0.0025 g |
| $(NH_4)_2SO_4$ | 0.5 g |
| Glucose | 1.8 g |
| After sterilization add: | |
| Chloramphenicol | 25 U |

Example 2

Tail-PCR

After screening *T. reesei* strains for improved cellulase production, improved strains were analyzed for genetic changes using mTAIL-PCR (modified thermal asymmetric interlaced-polymerase chain reaction). TAIL-PCR was performed using protocols modified from Sessions, et al. (The Plant Cell, 14:2985-2994, 2002) and Liu, et al. (Plant J., 8:457-463, 1995) and Liu and Whittier (Genomics, 25:674-661, 1995) using primers to the PZP vector and the gene of interest. Additionally, Southern blotting was performed to demonstrate that each of the new clones has only one copy of the modified gene.

Briefly, pyr4 specific primer and a pool of four arbitrary degenerate (AD) primers were used per round of TAIL-PCR cycling. The T-DNA primers used were as follows:

Random TAIL-PCR primers that were used:

| Name | ad1 |
|---|---|
| Synthesis | 50 nmole |
| Purification | Salt-Free |
| Sequence | NGTCGASWGANAWGAA |
| | [SEQ ID NO.: 7] |

| Name | ad2 |
|---|---|
| Synthesis | 50 nmole |
| Purification | Salt-free |
| Sequence | TGWGNAGSANCASAGA |
| | [SEQ ID NO.: 8] |

| Name | ad3 |
|---|---|
| Synthesis | 50 nmole |
| Purification | Salt-Free |
| Sequence | AGWGNAGWANCAWAGG |
| | [SEQ ID NO.: 9] |

| Name | ad4 |
|---|---|
| Synthesis | 50 nmole |
| Purification | Salt-Free |
| Sequence | WGTGNAGWANCANAGA |
| | [SEQ ID NO.: 10] |

The final concentrations of the pooled primers were AD1 3.0 µM, AD2 3.0 µM, AD3 3.0 µM and AD4 4.0 µM.

Specific pyr4 Primer
Reverse

| | | [SEQ ID NO.: 11] |
|---|---|---|
| 4rip | 5'AGCCGCGGCCTCCTGAT-'3 | |

| | | [SEQ ID NO.: 12] |
|---|---|---|
| 5rip | 5'GTCGGCGCTCAGGCACAGGTTGG-'3 | |

| | | [SEQ ID NO.: 13] |
|---|---|---|
| 6rip | 5'CGTCGCCGTCTCGCTCCTG-'3 | |

Nested Primer
Reverse

| | | [SEQ ID NO.: 14] |
|---|---|---|
| 8rip | 5'TGCGGGAGGAAGAGGAGTAGGAAC'3 | |

The tail-PCR procedure was performed as follows. (see, Sessions, et. al., 2002, The Plant Cell, vol. 14. pp. 2985-2994).

In hotstart tubes using pipette tips with cotton plugs:
Step 1.

| Distilled H20 | 34 uL |
|---|---|
| 10X buffer | 5 uL |
| 10 mM dNTP | 2 uL |
| specific pyr4 primer | 1 uL (50 pmole) |
| ad1 primer | 2 uL |
| ad2 primer | 2 uL |
| ad3 primer | 2 uL |
| ad4 primer | 2 uL |

Heat 95, 90 seconds, cool to 4° C.

Step 2.

| Distilled H20 | 43 uL |
| --- | --- |
| 10X buffer | 5 uL |
| genomic DNA | 1 uL (dilute our DNA 1/5 with H$_2$0) |
| Hercules polymerase | 1 uL |

Run the first PCR Program, round 1 (T1). Cycling parameters are given below.

Step. 3

| Distilled H20 | 34 uL |
| --- | --- |
| 10X buffer | 5 uL |
| 10 mM dNTP | 2 uL |
| specific nested pyr4 primer | 1 uL (50 pmole) |
| ad1 primer | 2 uL |
| ad2 primer | 2 uL |
| ad3 primer | 2 uL |
| ad4 primer | 2 uL |

Heat 95, 90 seconds, cool to 4° C.

Step 4.

| Distilled H20 | 39 uL |
| --- | --- |
| 10X buffer | 5 uL |
| DNA template | 5 uL (from step 2, after running T1) |
| Hercules polymerase | 1 uL |

Run a second PCR round (T2). Cycling parameters are given below.

Two rounds of mTAIL-PCR cycling were performed. Cycling parameters for the first round (T1) were (1) 94° C. for 2 min and 95° C. for 1 min; (2) 5 cycles of 94° C. for 30 s, 62° C. for 1 min, and 72° C. for 2.5 min, (3) 2 cycles of 94° C. for 30 s, 25° C. for 3 min (50% ramp), and 72° C. for 2.5 min (32% ramp); (4) 15 cycles of 94° C. for 10 s, 68° C. for 1 min, 72° C. for 2.5 min, 94° C. for 10 s, 68° C. for 1 min, 72° C. for 2.5 min, 94° C. for 10 s, 44° C. for 1 min and 72° C. for 2.5 min; and (5) 72° C. for 7 min.

Cycling parameters for the second round (T2) containing 8 rip as the nesting primer as well as the Ad pool of primers was as follows: (1) 94° C. for 3 min, (2) 5 cycles of 94° C. for 10 s, 64° C. for 1 min, and 72° C. for 2.5 min, (3) 15 cycles of 94° C. for 10 s, 64° C. for 1 min, and 72° C. for 2.5 min, 94° C. for 10 s, 64° C. for 1 min, 72° C. for 2.5 min, 94° C. for 10 s, 44° C. for 1 min, and 72° C. for 2.5 min, (4) 5 cycles of 94° C. for 10 s, 44° C. for 1 min, and 72° C. for 3 min; and (5) 72° C. for 7 min. Tail-PCR products were purified and sequenced by treatment with exonuclease 1 (2.5 U; Amersham) and shrimp alkaline phosphatase (0.5 U; Amersham; Piscataway, N.J.) for 20 min at 37° C. followed by 15 min at 80° C. Sequencing reactions were performed in a 384-well format using the 8rip primer and one-eighth of the suggested amount of BigDye terminators (Applied Biosystems; Foster City, Calif.) and run on a standard sequencer. Sequencing reactions were passed through a Sephadex G-50 matrix to remove salts and unincorporated due terminators. Resulting sequences were BLASTED against *T. reesei* genomic sequences at JGI *Trichoderma reesei* v. 1.0.

Example 3

Fungal Transformation Procedures

*Agrobacterium* inoculate was prepared as follows. Twenty-five ml of Minimal Medium (MM) in 250 ml flasks was inoculated with either a frozen stock of vector transformed *Agrobacterium* or inoculated directly from a fresh LA plate culture. The culture was then incubated at 28° C. with shaking until the culture became cloudy (overnight to several days time). Next, 10 ml was transferred to 50 ml of Induction Medium (IM) in 250 ml flasks. Staring OD was about 0.1 at 600 nm and cells were cultured until OD was between 0.4-0.8. A fresh fungal plate (e.g., *T. reesei*) was prepared by resuspending spores in 10 ml of sterile water.

Transformation of fungus (e.g., *T. reesei* and *Aspergillus niger*) was performed as follows. About 100 µl of *Agrobacterium* whole broth (OD 0.4-0.8 at 600 nm) was mixed with about 100 µl of fungal spores ($10^7$ sfu/ml) in a tube. One practiced in the art will realize that other rations of *Agrobacterium* to fungal spores will also produce satisfactory results. Next, 0.1 to 1.0 ml of the mix was plated onto induction plates containing nitrocellulose filters. Induction plates were supplemented with nutrients required by the fungi as needed to correct any auxotrophy present in the fungi. The plates were incubated at about 18-28° C. for about 24-48 hours for *T. reesei*. For *Aspergillus niger* the cultures was incubated at about 20-24° C. for about 20-24 hours. Next, the filters were transferred to selective medium (Vogels medium for *T. reesei* and minimal medium for *A. niger*). The medium was supplemented with 250 ppm carb to kill/inhibit *Agrobacterium* growth. The cultures were then incubated at 28° C. until growth is evident on the filter. This takes as long as one to two weeks. The transformants were transferred to selective medium when they were ready for further analysis.

Example 4

Toyama Screen

The Toyama screen was developed by Drs. Hideo and Nobuo Toyama from Miniamikyashu University in Japan. Toyama, H. and Toyama, N., *Successive construction of cellulase hyperproducers of Trichoderma using hyperpolyploids*. Appl. Biochem. Biotechnol. Spring 84-86:419-429, 2000. The method describe therein was modified from the original procedure to be more effective at improving Genencor's *Trichoderma reesei* cellulase production strains and to be a high through-put screen. This screen has been used successfully to isolate strains with improvements in both yield and productivity. Here, we used the screen to isolate strains 7p, 8k, 7E, 9G, 8Q and 203 from the parental strain. These strains show improved cellulase production over the parental *T. reesei* strain.

Mutagenized spores were prepared using insertional mutagenesis (as detailed in Example 2). An aliquot of the mutational libraries was frozen at −70° C. A viable spore count was determined and the remaining library was divided so that each aliquot contained about $10^6$ spores.

The Toyama screen medium was prepared an cooled to 55° C. in a water bath. In an 82 mm petri dish an aliquot was dispensed in a circle about ½ way from the center of the plates and the edge. Next, 10 ml of Toyama screening medium was carefully added to the culture plates and the plate was swirled so that the spores were dispersed in the middle of the plate but not dispersed al the way to the edges of the plate (see FIG. 3). Alternately, the spores may be spread out with a sterile loop before the addition of the Toyama medium. The medium was let harden for 5-10 minutes. Another 25 ml of medium was added to the plates and let harden. Next, another 10 ml of medium was added to the plates and let harden. The plates were incubated overnight The next day growth of the spores was examined using a dissecting microscope. Plates were checked every four hours. Isolates were collected as follows. Only the first 1-3 isolates that reached the surface of the agar were collected. Any colonies that came up around the edges of the plate (cheaters) were ignored. Isolates were collected using a sterile razor blade under the microscope being careful not to dig into the surface of the agar. The collected samples were placed onto PDA (potato-dextrose-agar; Difco, Gaithersburg, Md.) plates and incubated at 28° C. Once grown, the isolates were evaluated on acid swollen cellulose plates or were put directly into shaker flasks.

TABLE 3

Toyama Screening Medium

Make to one liter:

| | |
|---|---|
| 50X Vogels Stock Solution | 30 ml |
| Avicel | 0.5 g |
| Agar | 20 g |

50X Vogels Stock Solution

Using three glass containers separately add:

| | |
|---|---|
| $Na_3Citrate*2H_2O$ | 150 g |
| $MgSO_4*7H_2O$ | 10 g |
| $CaCl_2*2H_2O$ | 5 g |
| Dissolve in $diH_2O$ to | 300 ml |
| $KH_2PO_4$ | 250 g |
| Dissolve in $DiH_2O$ to | 500 ml |

TABLE 3-continued

| | |
|---|---|
| $NH_4NO_3$ | 100 g |
| Dissolve in $diH_2O$ to | 200 ml |
| Allow all components to clear in $diH_2O$. | |
| Combine all solutions and add with mixing: | |
| Vogels Trace Element Solution | 5 ml |
| Vogels Biotin Solution | 2.5 ml |

Vogels Biotin Solution

Make to one liter:

| | |
|---|---|
| d-biotin | 0.1 g |
| Dissolve in $diH_2O$ to | 1.0 L |

Vogels Trace Element Solution

Make to one liter:

| | |
|---|---|
| Citric Acid | 50 g |
| $ZnSO_4*7H_2O$ | 50 g |
| $Fe(NH_4)_2SO_4*6H_2O$ | 10 g |
| $CuSO_4*5H_2O$ | 2.5 g |
| $MnSO4*4H_2O$ | 0.5 g |
| $H_3BO_3$ | 0.5 g |
| $NaMoO_4*2H_2O$ | 0.5 g |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A *Trichoderma reesei* filamentous fungus having a mutation or deletion of part or all of a gene having the sequence of SEQ ID NO: 4, and said mutation or deletion results in the enhanced production of a desired polypeptide compared to the parent *T. reesei* filamentous fungus.

2. The filamentous fungus of claim 1, wherein said filamentous fungus is capable of expressing a heterologous protein.

3. The filamentous fungus of claim 1, wherein said heterologous protein is selected from the group consisting of hormones, enzymes, growth factors, and cytokines.

4. The filamentous fungus of claim 3 wherein said heterologous protein is an enzyme.

5. The filamentous fungus of claim 4 wherein said enzyme is selected from the group consisting of proteases, carbohydrases, lipases, isomerases, racemases, epimerases, tautomerases, mutases, transferases, kinases and phosphatases.

6. A method for the production of a heterologous protein in a transformed *Trichoderma reesei* host cell comprising:

growing a *T. reesei* host cell comprising a nucleic acid encoding said heterologous protein wherein said host cell contains a mutation or deletion of part or all of a gene having the sequence of SEQ ID NO: 4, wherein said mutation or deletion results in the enhanced production of the heterologous protein compared to a parent filamentous fungus, and wherein said growing of said host is under conditions suitable for the expression of said heterologous protein.

7. An isolated nucleic acid molecule having a truncation or mutation of the sequence of SEQ ID NO: 4, wherein the truncation or mutation reduces or eliminates expression of SEQ ID NO: 4 and wherein said nucleic acid molecule is capable of homologous recombination with a wild-type gene having the nucleotide sequence of SEQ ID NO: 4.

8. A vector comprising the nucleic acid molecule according to claim 7.

9. A host cell transformed with a vector according to claim 8.

* * * * *